United States Patent
Ikuno

(10) Patent No.: US 8,360,632 B2
(45) Date of Patent: Jan. 29, 2013

(54) THERMAL FATIGUE TESTING DEVICE AND RECORDING MEDIUM RECORDED WITH A PROGRAM

(75) Inventor: Hajime Ikuno, Seto (JP)

(73) Assignee: Kabushiki Kaisha Toyota Chuo Kenkyusho, Aichi-Gun (JP)

( * ) Notice: Subject to any disclaimer, the term of this patent is extended or adjusted under 35 U.S.C. 154(b) by 429 days.

(21) Appl. No.: 12/728,686

(22) Filed: Mar. 22, 2010

(65) Prior Publication Data
US 2010/0246632 A1 Sep. 30, 2010

(30) Foreign Application Priority Data
Mar. 24, 2009 (JP) ................................. 2009-071584

(51) Int. Cl.
*G01N 3/60* (2006.01)
(52) U.S. Cl. .......................................................... 374/57
(58) Field of Classification Search .................... 374/57; 73/865.6
See application file for complete search history.

(56) References Cited

U.S. PATENT DOCUMENTS

| | | | | |
|---|---|---|---|---|
| 4,787,752 A | * | 11/1988 | Fraser et al. | 374/45 |
| 4,793,716 A | * | 12/1988 | Wei et al. | 374/45 |
| 4,817,447 A | * | 4/1989 | Kashima et al. | 73/865.6 |
| 5,039,228 A | * | 8/1991 | Chalmers | 374/57 |
| 5,193,910 A | * | 3/1993 | Kinoshita | 374/45 |
| 5,707,147 A | * | 1/1998 | Kurkowski et al. | 374/1 |
| 5,967,660 A | * | 10/1999 | Akpan et al. | 374/57 |
| 5,980,103 A | * | 11/1999 | Ikuno et al. | 374/57 |
| 7,559,251 B2 | * | 7/2009 | Lee et al. | 73/808 |
| 7,690,839 B2 | * | 4/2010 | Ye et al. | 374/57 |
| 2007/0127544 A1 | * | 6/2007 | Huang | 374/57 |
| 2010/0046575 A1 | * | 2/2010 | Hebert et al. | 374/57 |
| 2010/0329300 A1 | * | 12/2010 | Saarinen et al. | 374/57 |

FOREIGN PATENT DOCUMENTS

| | | |
|---|---|---|
| JP | A-60-249035 | 12/1985 |
| JP | U-03-078244 | 8/1991 |
| JP | A-07-020031 | 1/1995 |
| JP | A-07-270303 | 10/1995 |
| JP | A-09-178639 | 7/1997 |

OTHER PUBLICATIONS

Office Action issued in Japanese Application No. 2010-053138 dated Aug. 7, 2012 (w/ English Translation).

* cited by examiner

*Primary Examiner* — Christopher Fulton
(74) *Attorney, Agent, or Firm* — Oliff & Berridge, PLC

(57) ABSTRACT

A thermal fatigue testing device that includes a gas cooling component, a tube member, and a heat generating body is provided. The gas cooling component cools a blown gas to a predetermined temperature or less, and that is provided with a heat insulating member at an outer side surface thereof. The tube member has a gas flow path formed therein from a first end to a second end, is provided at an outer side surface thereof with a heat radiating portion from the second end to a first intermediate portion, and is connected with the gas cooling component at the first end side. A test body is arranged at the second end side. The heat generating body is provided in the gas flow path between the first end and a second intermediate portion and heats a gas flowing through the gas flow path.

15 Claims, 3 Drawing Sheets

THERMAL FATIGUE TESTING DEVICE AND RECORDING MEDIUM RECORDED WITH A PROGRAM

BACKGROUND OF THE INVENTION

1. Field of the Invention

The present invention relates to a thermal fatigue testing device and a recording medium recorded with a program.

2. Description of the Related Art

Conventionally, as a comparatively simple thermal fatigue testing method merely for evaluating a thermal fatigue life, a method is known that evaluates a thermal fatigue life by generating a temperature distribution at a test piece (test body) itself, and breaking the thermal fatigue test piece by a generated heat strain (for example, see Japanese Patent Application Laid-Open (JP-A) No. 60-249035). However, this method has a problem in that an entire test piece, which has a shape resembling an abacus bead, is heated and cooled, whereby states of a heat stress and a heat strain that accompanies a temperature cycle become complex, and it is not possible to quantitatively evaluate a thermal fatigue life.

In this regard, a thermal fatigue testing method and a thermal fatigue testing device that can address this problem have been proposed (for example, see JP-A No. 7-20031).

JP-A No. 7-20031 discloses a simple thermal fatigue testing method and thermal fatigue testing device which can be used in the evaluation of the thermal fatigue resistance of a metal material, a ceramic or the like, and in particular a light metal material. JP-A No. 7-20031 discloses a technique of performing a thermal fatigue test in which a test piece is held by a holder having a thermal expansion coefficient different to that of the test piece, and subjecting the entire test piece and holder to heating and cooling, and applying a desired strain to the test piece using the difference in thermal expansion between the holder and test piece. This technique is advantageous in terms of equipment cost and the like, since it is possible to apply a mechanical strain to a test piece without having to use an actuator. However, since a heating component and a cooling component are provided separately, there remains room for improvement in terms of reducing the size and complexity of a device. Further, since the entire test piece and holder are heated and cooled, a temperature non-uniformity is generated according to the thermal capacity of each component, and it is difficult to intentionally apply a desired temperature distribution to a test piece.

In order to address these issues, a thermal fatigue testing device that integrates a heating component and a cooling component such that it is smaller and simpler, and a thermal fatigue testing method that makes a temperature distribution of a test piece uniform, and that enables intentional application of a desired temperature distribution, have been proposed (for example, see Japanese Patent Application Laid-Open (JP-A) No. 9-178639).

JP-A No. 9-178639 discloses a thermal fatigue testing method that performs heating and cooling of a test piece (test body) using an air heater. Further, JP-A No. 9-178639 discloses a thermal fatigue testing device in which air is supplied by plural nozzles (six nozzles in JP-A No. 9-178639) according to a test piece and a holder that holds the test piece, thereby heating the test piece uniformly. JP-A No. 9-178639 discloses a thermal fatigue testing device that integrates a heating component and a cooling component to achieve an advantageous thermal fatigue testing device which is smaller and simpler, and discloses an advantageous thermal fatigue testing method that makes a temperature distribution of a test piece uniform, and enables intentional application of a desired temperature distribution.

Although the thermal fatigue testing device and thermal fatigue testing method disclosed in JP-A No. 9-178639 is advantageous as described above, in the thermal fatigue testing device disclosed in JP-A No. 9-178639, the air temperature used in the heating and cooling of the test piece is at or above room temperature, and it is difficult to reduce this air temperature to room temperature or less. Moreover, in the thermal fatigue testing device disclosed in JP-A No. 9-178639, since a large number of nozzles are necessary for use with respect to the test piece, the device structure is complex, and a large installation area is necessary in order to employ multiple test units. Considering the above, there is room for improvement of the thermal fatigue testing device and thermal fatigue testing method disclosed in JP-A No. 9-178639.

JP-A No. 9-178639 includes disclosure of temperature control, but there is a need for a faster, more accurate and more stable temperature control.

SUMMARY OF THE INVENTION

An aspect of the present invention provides a thermal fatigue testing device that includes: a gas cooling component that cools a blown gas (such as air, nitrogen or carbon dioxide) to a predetermined temperature or less, and that is provided with a heat insulating member at an outer side surface thereof; a tube member, having a gas flow path formed therein from a first end to a second end, and provided at an outer side surface thereof with a heat radiating portion from the second end to a first intermediate portion, and being connected with the gas cooling component at the first end side, and a test body being arranged at the second end side; and a heat generating body provided in the gas flow path between the first end and a second intermediate portion, that heats a gas flowing through the gas flow path.

DETAILED DESCRIPTION OF THE INVENTION

An embodiment of the thermal fatigue testing device of the present invention is explained in detail below with reference to the drawings.

Figure 1:
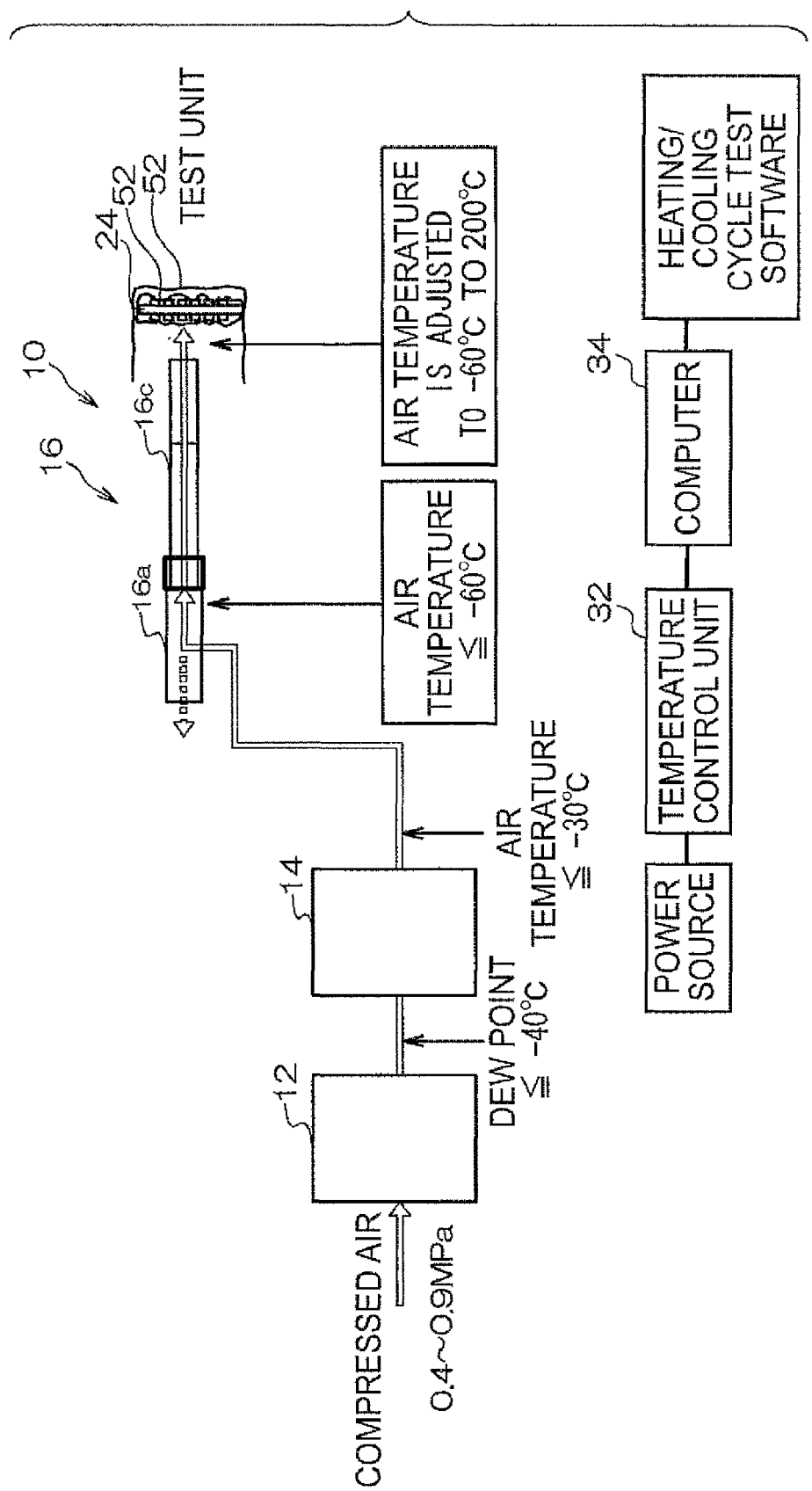
FIG. 1 shows a thermal fatigue testing device according to an embodiment of the present invention.
Figure 2:
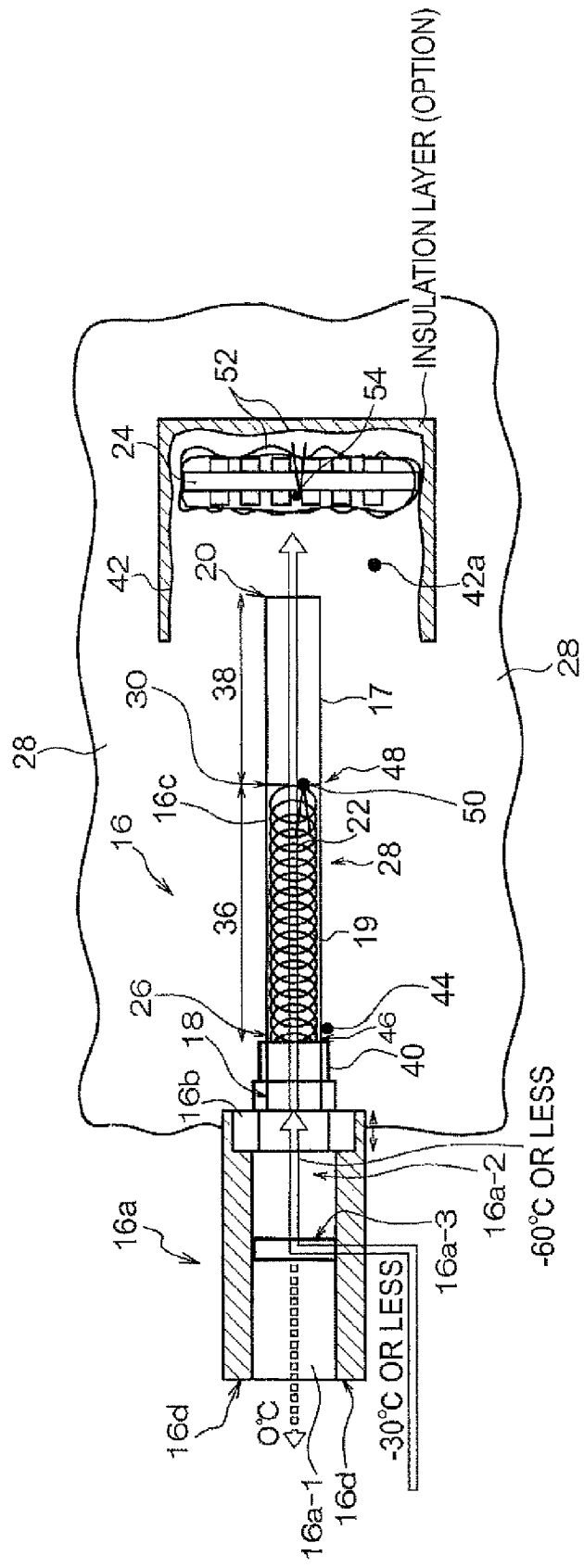
FIG. 2 is a detailed view of an area near a heating/cooling device of a thermal fatigue testing device according to an embodiment of the present invention.

The following is an explanation of the thermal fatigue testing device according to the present embodiment. As shown in FIGS. 1 and 2, the thermal fatigue testing device 10 according to the present embodiment is provided with an (adsorption) air dryer 12, a (two-stage) cold insulator 14, a heating/cooling device 16, a temperature control unit 32, a computer 34 and a constant-temperature portion 42.

Air dryer 12 generates and blows dry air which is at around −40° C. below a dew point or less, from compressed air which is supplied from an air compressor or the like at a pressure of around 0.4 MPa to around 0.9 MPa.

In the present embodiment, air is used as an example of a gas; however, the present invention is not limited thereto, and any gas may be used, such as nitrogen or carbon dioxide.

Cold insulator 14 cools air blown from air dryer 12 such that it is a low temperature air with a temperature of around −30° C. or less, and blows the air to heating/cooling device 16.

Heating/cooling device 16 is provided with a vortex tube 16a, a refrigeration portion 16b and an air heater 16c. Further, heating/cooling device 16 is an example of a gas supply component of the present invention.

Vortex tube 16a cools the low temperature air blown from cold insulator 14 to a predetermined temperature (for example, −60° C.) or less. Specifically, vortex tube 16a includes a hot air tube 16a_1 that extends in one direction, a cold air ejection opening 16a_2 that extends in the opposite direction, and a generator 16a_3 between the two. When generator 16a_3 blows a swirling air flow at a high speed into hot air tube 16a_1, a temperature difference is generated owing to a pressure gradient that occurs therein, hot air is ejected from a leading end of hot air tube 16a_1, and simultaneously cold air, which flows backwards in hot air tube 16a_1, is ejected from cold air ejection opening 16a_2. Super-cooled air can be obtained owing to vortex tube 16a configured in this manner.

Vortex tube 16a is provided with a heat insulating member 16d (insulation layer) at an outer side surface thereof, and is covered with heat insulating member 16d. Owing to heat insulating member 16d covering vortex tube 16a, it is possible to suppress the influence of a temperature outside vortex tube 16a on the temperature of air cooled by vortex tube 16a, and thereby it is possible to cool air more quickly and to a lower temperature. Vortex tube 16a is an example of a gas cooling component of the present invention.

Refrigeration portion 16b has a function of keeping air (cooled air) ejected (blown) from vortex tube 16a cold.

By passing through refrigeration portion 16b, a temperature distribution of air is reduced, and it is possible to obtain a super-cooled air flow at a stable temperature that does not change greatly over time.

Air heater 16c is provided with a tube member 17 and a heat generating body 19. Further, air heater 16c is an example of a heating component of the present invention.

At an inner portion of tube member 17, a gas flow path 22 is formed from a first end 18 to a second end 20, and is connected at a first end 18 side to cold air ejection opening 16a_2 of vortex tube 16a via refrigeration portion 16b. As shown in the figures, a test body 24 is provided at a second end 20 side such that air may be blown thereon from second end 20.

Tube member 17 is provided with a heat radiating portion 28 (heat radiating layer) at an outer side surface, that extends from second end 20 to a first intermediate part 26. In the present embodiment, an example of heat radiating portion 28 is the atmosphere. It is preferable that heat radiating portion 28 is provided at 80% or more of the entire area of an outer side surface of tube member 17 (outer side surface of gas flow path 22).

It is preferable that tube member 17 includes a material that can permeate light and heat, but that has a low thermal conductivity, such as glass. Thereby, heat loss from tube member 17 can be suppressed and fast and efficient heating can be realized. As a material of the glass (glass tube), quartz is preferable since it has a low thermal expansion coefficient. Thereby, it is not susceptible to thermal strain during heating and cooling, and is not readily broken.

As shown in the figures, heat generating body 19 is provided in gas flow path 22 between first end 18 and a second intermediate part 30 (between first end 18 and a second intermediate part 30 and in gas flow path 22), such that it may heat air that flows through gas flow path 22. A heat generating temperature of heat generating body 19 is controlled by temperature control unit 32 which is explained below. In the present embodiment, explanation is made of an example using a heater as heat generating body 19.

In the present embodiment, explanation is given of an example in which tube member 17 which contains heat generating body 19 is configured as a quartz tube. As shown in FIG. 2, heating/cooling device 16 may be considered to be provided with a heating zone 36 at which heat generating body 19 is provided in gas flow path 22, which is an area (zone) in gas flow path 22 in which air from first end 18 to second end 20 may be heated, and with a uniform heating zone 38 at which heat generating body 19 is not provided in gas flow path 22, which is an area in gas flow path 22 from second intermediate part 30 to second end 20.

In the present embodiment, a protection tube 40 that holds and protects tube member 17 has a length of about ¼ of the length of heating zone 36. In the example shown in FIG. 2, the length of protection tube 40 extends from first end 18 to first intermediate part 26. Therefore, heat radiating portion 28 is provided at an outer side surface from second end 20 to first intermediate part 26. As described above, in the present embodiment an example of heat radiating portion 28 is the atmosphere. Since protection tube 40 functions as a heat storing member, it is preferable that it is short. Accordingly, the length of protection tube 40 may be ¼ the length of heating zone 36. The specific reason for this is that, since heat radiating portion 28 is provided at an outer side surface from second end 20 to first intermediate part 26, compared to a case in which a heat storing member is provided at this outer side surface, it is possible to accelerate an increase or a decrease in a temperature of air in gas flow path 22 which is to be changed by heat generating body 19. For example, when air cooled by vortex tube 16a (obtained super-cooled air) is not heated by heat generating body 19, then after blowing the cooled air to test body 24, in order to increase the temperature of air blown to test body 24, air cooled by vortex tube 16a is heated by heat generating body 19, and if a heat storing member is provided at an outer side surface, since the temperature of the heat storing member remains low, an increase in temperature of air blown to test body 24 is suppressed and the speed at which a temperature increases is reduced. By contrast, according to heating/cooling device 16 of thermal fatigue testing device 10 of the present embodiment, since heat radiating portion 28 is provided at an outer side surface from second end 20 to first intermediate part 26, the suppression of an increase in temperature of air blown to test body 24 can be eliminated. As a result, owing to heating/cooling device 16 of thermal fatigue testing device 10 of the present embodiment, control can be performed such that a change in temperature of air blown to test body 24 is accelerated.

In heating/cooling device 16 of thermal fatigue testing device 10 according to the first embodiment, since heat generating body 19 is provided in gas flow path 22 between first end 18 and second intermediate part 30, an air flow is obstructed and a flow speed distribution increases, thereby generating a large temperature distribution at second intermediate part 30, but since heat generating body 19 is not provided from second intermediate part 30 to second end 20 in gas flow path 22 (at a uniform heating zone 38), there is no member that obstructs an air flow, and a flow speed distribution decreases, and since a heat exchange occurs between air at different temperatures in gas flow path 22 from second intermediate part 30 to second end 20, an air temperature distribution at second end 20 is reduced. As a result, it is possible to perform uniform and stable heating or cooling with respect to test body 24.

Further, in the present embodiment, a generally used overheating sensor 44 that detects an abnormal temperature of heat generating body 19 for preventing abnormal overheating of heat generating body 19 is provided at an upstream side in an air blowing direction of heating zone 36 (in the example shown in FIG. 2, inlet 46 of heating zone 36).

The main cause of abnormal overheating is thought to be a decrease in an air flow amount. In particular, a decrease in an air flow amount greatly affects an area near air inlet 46, and an increase in temperature near inlet 46 may be very large. Therefore, by providing overheating sensor 44 at inlet 46, an overheating prevention circuit or computer 34 can control heat generating body 19 via temperature control unit 32 such that heating can be stopped soon after an abnormal temperature is generated.

In heating/cooling device 16 of thermal fatigue testing device 10 of the present embodiment, it is possible to blow air to test body 24 having a temperature within a range from a temperature cooled to a predetermined temperature or less, to a temperature of air heated by heat generating body 19.

A heater temperature sensor 50 is provided at a final end portion 48 of heating zone 36 (a final end portion of heat generating body 19). In the following, the expression "heat generating body final end portion" may be used to mean "final end portion of heat generating body 19". Heater temperature sensor 50 detects a temperature of air at final end portion 48 (heat generating body final end portion 48) of heat generating body 19 (a heater), and outputs a detection signal representing the detected temperature to temperature control unit 32.

Temperature control unit 32, based on a temperature indicated by information indicating a target air temperature of heat generating body final end portion 48 input from computer 34, and an air temperature of heat generating body final end portion 48 indicated by a detection signal from heater temperature sensor 50, performs a feedback control, and controls a heating of heat generating body 19 (a heat generation amount) such that an air temperature of heat generating body final end portion 48 becomes the temperature indicated by the information input from computer 34. In other words, computer 34 can control the air temperature of final end portion 48 via temperature control unit 32.

Computer 34, using a heating/cooling cycle test software, and based on test data, performs temperature control with respect to heat generating body 19 (specifically, a temperature of heat generating body 19) via temperature control unit 32 such that test body 24 becomes a target temperature indicated by the test data. The test data is a time-series data of target temperatures for changing the temperature of test body 24 to temperatures between predetermined upper and lower limits according to a time-series. A detailed explanation of a specific temperature control process by which temperature control is performed is given below.

Computer 34 controls the entirety of thermal fatigue testing device 10, and is provided with a memory, a CPU (Central Processing Unit), and I/O (Input/Output) ports. The memory, CPU and I/O ports are connected to each other via a bus.

The memory, as a recording medium, stores a basic program such as an OS. The memory also stores various programs for executing various processing routines including a temperature control process, a deviation calculation process, and various other processes, which are explained in detail further below.

The CPU reads each program from the memory and executes each of the above processes. The memory also temporarily stores various types of data.

Figure 3:
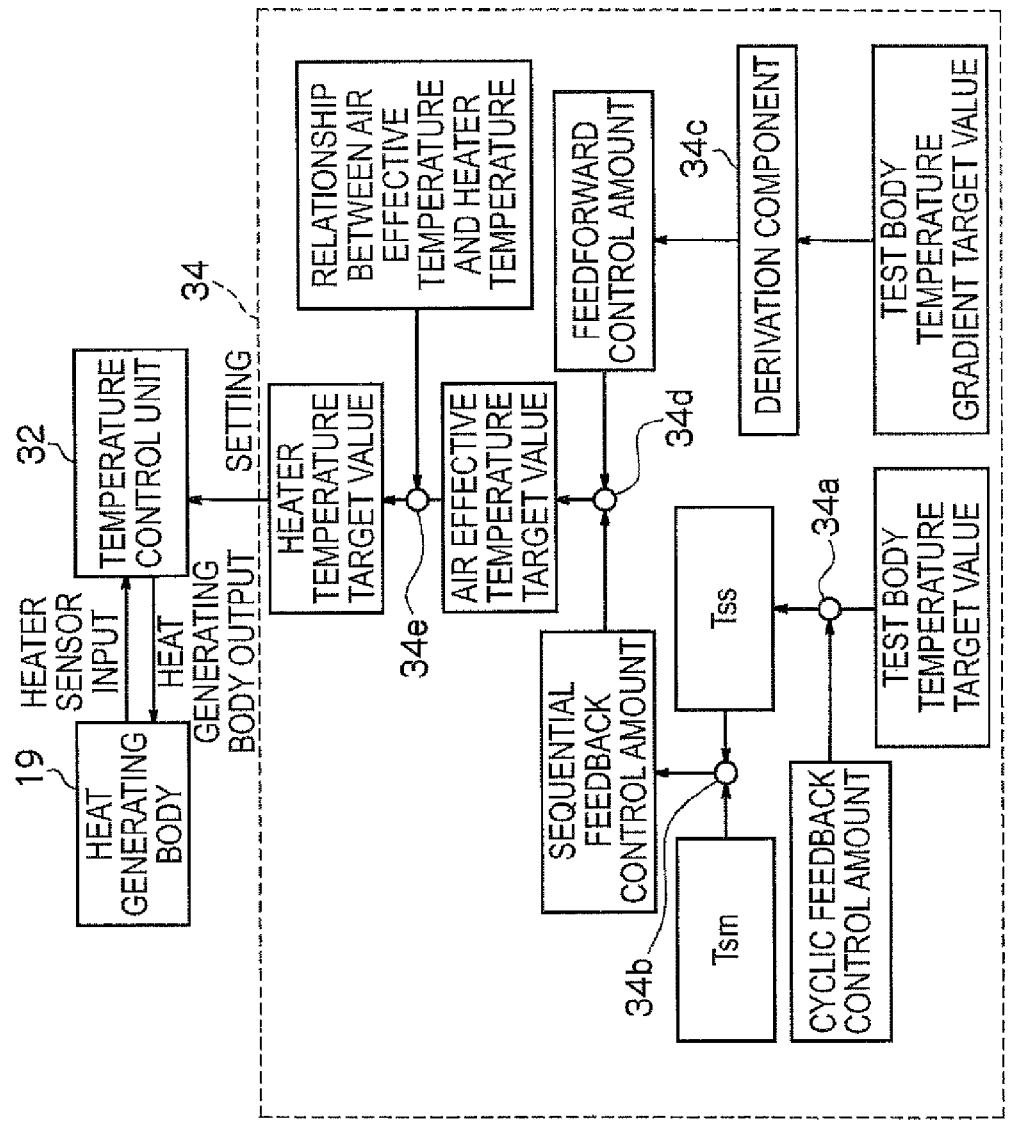
FIG. 3 is a function block drawing of a thermal fatigue testing device according to an embodiment of the present invention.

Computer 34 may be expressed as function blocks of a temperature control process as follows. As shown in FIG. 3, computer 34 may be expressed as a correction component 34a, a correction value calculation component 34b, a derivation component 34c, a target temperature calculation component 34d, and a heat generating body temperature derivation component 34e.

As shown in FIG. 2, constant-temperature portion 42 has an open end at a second end 20 side, and is formed of a high thermal conductivity member 52 (a high thermal conductivity film), which has a thermal conductivity at or above a predetermined value. Constant-temperature portion 42 is formed around test body 24 such that air blown from second end 20 to test body 24 is trapped around test body 24. As a material of high thermal conductivity member 52, aluminum foil or copper foil may be used.

As shown in the figure, test body 24 according to the present embodiment may be covered by high thermal conductivity member 52. A high thermal conductivity member 52 that surrounds a constant-temperature zone 42a, and a high thermal conductivity member 52 that surrounds test body 24 may be a metal foil, such as an aluminum foil or a copper foil, having a thickness of around 11 µm. Further, in order to distinguish between the high thermal conductivity member 52 that surrounds test body 24 and the high thermal conductivity member 52 that surrounds a constant-temperature zone 42a, the high thermal conductivity member 52 that surrounds test body 24 is designated as high thermal conductivity member 52a, and the high thermal conductivity member 52 that surrounds a constant-temperature zone 42a is designated as high thermal conductivity member 52b.

Temperature-adjusted air is blown to constant-temperature zone 42a in constant-temperature portion 42, and since this air is temporarily trapped in a limited space, a temperature in constant-temperature zone 42a can be quickly and efficiently heated or cooled to a temperature of the blown air. In other words, constant-temperature portion 42 is formed such that test body 24 is surrounded with high thermal conductivity member 52b, which has a thermal conductivity at or above a predetermined value, such that air blown to test body 24 from second end 20 is temporarily trapped around test body 24. Moreover, a temperature of a wall surface in constant-temperature zone 42a for transmitting heat quickly via high thermal conductivity member 52b, which forms the wall surface, becomes uniform, and temperature distributions of the wall surface and constant-temperature zone 42a become constant. As a further effect of the invention, since an ambient temperature at a peripheral portion of test body 24 to which blown air does not readily reach and at a part of test body 24 at a side opposite to a second end 20 side to which air is blown, and the like, are quickly made substantially the same as the temperature of the blown air, a temperature distribution of the entirety of test body 24 can be made further uniform. This effect is particularly advantageous when test body 24 is large, and high thermal conductivity member 52a surrounding (covering) test body 24 alone is not sufficient to heat test body 24 uniformly.

Since uniform heating can be performed more quickly when the heat capacitance of high thermal conductivity member 52b that surrounds constant-temperature zone 42a is low, it is sufficient to provide high thermal conductivity member 52b as a film of one layer. If the strength or rigidity of high thermal conductivity member 52b that surrounds constant-temperature zone 42a is insufficient, a multilayer structure may be provided. It is preferable that the majority of an outer side of high thermal conductivity member 52b that surrounds constant-temperature zone 42a is covered with a material that is not covered with an insulating layer, and is an insulating and heat radiating layer which is connected with an outer atmosphere, such as air. Thereby, it is possible for high thermal conductivity member 52b to be heated and cooled faster and more uniformly.

It is also preferable if the majority of an outer side of high thermal conductivity member 52b that surrounds constant-temperature zone 42a is covered with an insulating material. Thereby, since it is possible to prevent heat radiating from high thermal conductivity member 52b, a uniform heating property of high thermal conductivity member 52b is improved, and a temperature distribution of constant-temperature zone 42a can become more uniform, and thereby a temperature distribution of test body 24 can become more uniform. Further, it is also preferable that a gap layer of a gaseous body such as air is not provided between high thermal conductivity member 52b and the insulating material covering the outer side of high thermal conductivity member 52b, and for this reason it is preferable that high thermal conductivity member 52b is attached to the insulating material. A gap layer would impede heat radiation from high thermal conductivity member 52b, and thereby impede fast heating and cooling of high thermal conductivity member 52b. By attaching the insulating material to high thermal conductivity member 52b, a gap is not present, and fast heating and cooling becomes possible.

An example of an insulating material that covers an outer side of high thermal conductivity member 52b that surrounds constant-temperature zone 42a is given in the following. The insulating material preferably has a thermal conductivity of 0.2 (W/m·K) or less, and more preferably a thermal conductivity of 0.05 (W/m·K) or less. The insulating material preferably has a porous structure having holes therein, such as a resin, a ceramic material, fiberglass, a natural fiber or the like. Specific examples thereof include urethane foam, phenol foam, polystyrene foam, glass wool, rockwool, cellulose fiber or ceramic board. The insulating material may be about 2 mm thick or greater, and is preferably about 5 mm thick or greater. Moreover, an insulating material such as that described here may be used for insulating material (insulating layer) 16d described above.

It is preferable that the material of a holder that holds high thermal conductivity member 52b that surrounds constant-temperature zone 42a is a low thermal conductivity material and an insulating material such as a resin. A high thermal conductivity material may also be used, if the holder has a thin rod shape such as a wire, which has a low heat capacitance and by which a contact area with high thermal conductivity member 52b that surrounds constant-temperature zone 42a can be reduced. The same applies to a holder that holds test body 24 which is surrounded by high thermal conductivity member 52a. However, if a holder is arranged between high thermal conductivity member 52a and test body 24, the holder is preferably a high thermal conductivity material. For example, specific preferable holders include a foil, a thin plate, a wire, a wire mesh, or a rod or the like of a high thermal conductivity material such as aluminum or copper.

Owing to the above configuration, since heat of air blown on test body 24 is transmitted to the entirety of test body 24 quickly and uniformly, it is possible to heat or cool the entirety of test body 24 quickly and uniformly simply by blowing air to a portion of test body 24. This effect is considerable, and since the temperatures of a side of test body 24 to which air is blown, and a side of test body 24 to which air is not blown can be made uniform quickly, it is possible to heat or cool quickly and uniformly a large test body 24 by blowing air only from one direction. Since there is no need to blow air from plural directions, it is possible to simplify a device configuration.

As a high thermal conductivity material used for high thermal conductivity member 52a and high thermal conductivity member 52b and a holder that holds test body 24, a high thermal conductivity metal such as aluminum or copper is preferable. A carbonaceous high thermal conductivity material may also be used. The material preferably has a thermal conductivity of 100 (W/m·K) or greater, and more preferably 200 (W/m·K) or greater. Since a metal has excellent ductility, it is advantageous in that it can be easily formed so as to conform to the shape of test body 24 and constant-temperature zone 42a, and since it is also tough, it is stable and can be used over a long time. The purity of the aluminum or copper is preferably 90% or more, and more preferably 99% or more. A higher purity increases thermal conductivity, and also results in excellent ductility and formability.

High thermal conductivity member 52a is preferably a foil having a thickness of 50 μm or less, and more preferably a foil having a thickness of 20 μm or less. Since a thinner foil facilitates forming, it does not apply a load to test body 24, and can be easily formed to conform to a surface shape of test body 24 and cover test body 24. The optimal thickness is around 10 μm (from 7 μm to 15 μm). If the foil is thinner than this, it becomes weak, and a film is readily broken; additionally, manufacturing costs thereof are high and so a thinner foil is not preferable. A metal foil is optimal since it has excellent manufacturability, ductility and toughness.

High thermal conductivity member 52a is effective as a single film. However, a structure including multiple layers of films is more preferable. Thereby, since a load of the film may be reduced and the film can be more freely shaped, the film does not apply a substantial load to test body 24, and high thermal conductivity member 52a can be made to conform to a surface shape of test body 24 and cover test body 24. Additionally, by adjusting the number of film layers, the film can achieve an appropriate heat capacitance, and owing to a heat storage effect, a heat transfer to test body 24 can be performed smoothly, and it is possible to perform a faster and more uniform heating and cooling of test body 24.

As a material of high thermal conductivity member 52b, it is preferable to use the material described above for high thermal conductivity member 52a for substantially the same reasons. However, it is preferable that the material for high thermal conductivity member 52b is provided as a single layer and slightly thicker than high thermal conductivity member 52a. A thickness of around 1 mm or less is preferable, around 0.1 mm or less is more preferable, and around 30 μm (from 20 μm to 50 μm) is optimal. If the material is thinner than this, strength decreases and the material is more readily broken when used over a long period of time. In addition, since a thinner film has a lower heat storage capacity, a heat storage amount is reduced and a uniform heating effect may be insufficient. On the other hand, since high thermal conductivity member 52b is merely arranged around constant-temperature zone 42a, it may be made thicker than high thermal conductivity member 52a since this allows the formation process thereof to be simpler.

A temperature sensor 54 for detecting a temperature of test body 24 is attached at test body 24. Temperature sensor 54 is connected to computer 34 via temperature control unit 32, and detects a temperature of test body 24, and outputs a signal indicating the temperature of test body 24 to computer 34.

Temperature sensor 54 is an example of a test body temperature detecting component of the present invention.

An operation of computer 34 is described in the following. First, at correction component 34a, in accordance with Formula (1) and Formula (2), and based on test data and a deviation Esp calculated by a deviation calculation process explained in detail below, a current target temperature (target value) Tsv of test body 24 is corrected based on a first correction value, m·Esp (=ΔTsc), which is determined based on deviation Esp. A corrected target value (corrected target temperature) is Tsv+ΔTsc (=Tss).

$$\Delta Tsc = m \cdot Esp \quad (1)$$

$$Tss = Tsv + \Delta Tsc \quad (2)$$

Where m is a correction coefficient and is from 0 to 1. The above deviation Esp may be a cyclic feedback control amount.

A deviation calculation process is described in the following. The deviation calculation process is executed at regular intervals of a predetermined number of cycles by a CPU of computer 34. In the deviation calculation process, based on time-series data of target temperatures used for changing a temperature of test body 24, which is a test data, to between predetermined upper and lower limits according to a time-series, at least one of a deviation Esp_h between an upper limit temperature of test body 24 indicated by a detection signal from temperature sensor 54 and an upper limit temperature of the target temperature indicated by a time-series data or a deviation Esp_1 between a lower limit temperature of test body 24 indicated by a detection signal from temperature sensor 54 and a lower limit temperature of the target temperature indicated by a time-series data, is calculated as a deviation Esp.

Correction value calculation component 34b, according to Formula (3) and Formula (4), and based on a deviation between a temperature Tsm of test body 24 represented by a detection signal from temperature sensor 54 and a corrected target temperature Tss (Tss−Tsm (=En)), calculates a second correction value Mn (=f(En)) for further correcting target temperature Tss. Mn may be a sequential feedback control amount.

$$En = Tss - Tsm \quad (3)$$

$$Mn = f(En) \quad (4)$$

Where f(x) is a function (such as f(x)=x) for performing feedback control, and is preferably a function for performing a PID control.

Derivation component 34c, according to Formula 5, and based on a relationship obtained in advance through experimentation that relates a temperature difference between a temperature of test body 24 and a temperature of air blown to test body 24, to a temperature gradient of target temperatures represented by a time-series data of target temperatures, derives a temperature difference Sn between a temperature of test body 24 and a temperature of air blown to test body 24, that corresponds to a temperature gradient Vsv of a target temperature represented by a time-series data of a current target temperature.

$$Sn = Pp \cdot Vsv \quad (5)$$

Where Pp is a coefficient obtained based on a relationship obtained in advance through experimentation that relates a temperature difference between a temperature of test body 24 and a temperature of air blown to test body 24, to a temperature gradient of a target temperature indicated by a time-series data of a target temperature. Sn may be a feed-forward control amount.

Target temperature calculation component 34d, according to Formula (6), and based on corrected target temperature Tss, second correction value Mn, and temperature difference Sn, calculates a target temperature Ta of air blown to test body 24.

$$Ta = Sn + Mn + Tss \quad (6)$$

Ta is an implementation air temperature target value.

Heat generating body temperature derivation component 34e, according to Formula (7), and based on a relationship obtained in advance through experimentation that relates a temperature of air blown to test body 24 to a temperature of air at heat generating body final end portion 48, and further based on a target temperature Ta, calculates an air temperature Th at heat generating body final end portion 48 that corresponds to target temperature Ta.

$$Th = g(Ta) \quad (7)$$

Where g(x) is a function determined in advance that represents a temperature of heat generating body 19 when x is a temperature of air blown to test body 24. Th may be a target temperature of a heater.

Heat generating body temperature derivation component 34e controls heat generating body 19 via temperature control unit 32 so that it becomes derived temperature Th. Specifically, heat generating body temperature derivation component 34e inputs information indicating temperature Th to temperature control unit 32. Thereby, temperature control unit 32 controls a heating of air at heat generating body final end portion 48 such that a temperature of air at heat generating body final end portion 48 becomes the temperature Th indicated by the information input from computer 34 (more specifically, temperature control unit 32 controls a heat generation amount of heat generating body 19).

The above describes thermal fatigue testing device 10 according to the present embodiment. The thermal fatigue testing device 10 of the present embodiment derives a temperature difference Sn between a temperature of test body 24 and a temperature of air blown to test body 24 that corresponds to a temperature gradient Vsv. Then, a target temperature Ta of air blown to test body 24 is calculated taking into consideration temperature difference Sn, and, based on a previously obtained relationship between a temperature of air blown to test body 24 and a temperature of air at heat generating body final end portion 48, and also based on target temperature Ta, an air temperature Th of heat generating body final end portion that corresponds to target temperature Ta is derived, and a heat generation amount of heat generating body 19 is controlled so as to achieve derived temperature Th. Since a target temperature Ta of air blown to test body 24 is calculated from a target temperature Tss of test body 24, and an air temperature Th of heat generating body final end portion 48 is derived from a previously obtained relationship between a temperature of air blown to test body 24 and a temperature of air at heat generating body final end portion 48, and the heat generation amount of heat generating body 19 is controlled accordingly, a target temperature of test body 24 can be accurately implemented, and a temperature of test body 24 can quickly and accurately become a target temperature represented by a time-series data of a target temperature. Moreover, since a movement of heat that causes a temperature change of test body 24 is in principle generated in proportion to a difference between a temperature of air blown to test body 24 and a temperature of test body 24, by using a temperature of air blown to test body 24 as a physically significant intermediate parameter, temperature control is performed based on principles, and thereby stable temperature control can be realized.

Conventionally, when a test body is to be heated and cooled, a heating device and a cooling device are installed separately, and heating by the heating device and cooling by the cooling device are performed by switching in turns between the two. This is because, if both devices are used simultaneously, there is a large amount of heat loss, and it is not easy to perform a temperature adjustment efficiently or quickly. In particular, when a cooling device is used to perform cooling to a temperature below room temperature, there may be a large decrease in efficiency.

However, in thermal fatigue testing device 10 according to the present embodiment, a heating device (air heater 16c or the like) and a cooling device (vortex tube 16a or the like) by which fast temperature adjustment can be performed are provided directly connected to each other, and temperature-adjusted air is blown directly to test body 24 arranged near a final end of the heating device. Thereby, owing to thermal fatigue testing device 10 of the present embodiment, heat loss can be substantially prevented, and it is possible for the first time to realize fast and uniform heating or cooling of a test body. Specifically, the present embodiment uses vortex tube 16a or the like as a cooling device that can perform a fast temperature adjustment, and uses a heater (such as air heater 16c) that has a high heat exchange efficiency and that radiates a large amount of heat as a heating device that can perform a fast temperature adjustment. Further, by adjusting cooled air obtained from vortex tube 16a to an arbitrary temperature by air heater 16c, an exceptional effect is achieved; namely, temperature adjustment within a large temperature range from a temperature lower than room temperature to a high temperature, of 200° C. or greater can be performed accurately only by adjusting an output of air heater 16c. This effect cannot be realized with a combination of a general cooling device that performs temperature adjustment slowly and a general heater that has low heat exchange efficiency and retains a large amount of heat. Further, even if the order of communication is reversed and vortex tube 16a is arranged after air heater 16e, a highly accurate temperature adjustment cannot be realized.

Further, in thermal fatigue testing device 10 according to the present embodiment, uniform heating zone 38 and a refrigeration zone may be provided in heating/cooling device 16; thereby, a more efficient and more uniform heating or cooling may be realized.

The above describes a thermal fatigue testing device in which heating/cooling device 16, test body 24 and constant-temperature portion 42 are a single group; however, the present invention is not limited thereto. The present invention may include a multiple element system provided with plural groups each including a heating/cooling device 16, a test body 24 and a constant-temperature portion 42. In a multiple element system having the configuration explained in the above embodiment, plural heating/cooling devices 16 and test bodies 24 may be arranged side by side, and operation spaces for exchanging test bodies 24 can be arranged together at a side of test body 24 opposite to a heating/cooling device 16 side, thereby achieving the effect of allowing test operations to be performed efficiently in a small space.

In the present embodiment of the present invention, air is given as an example of a gas; however, the present invention is not limited thereto. A gas such as nitrogen or carbon dioxide may be used, or gas other than these may be used. As the gas, a gas suitable for heating and cooling a test body when blown thereto is preferable.

The present embodiment is an example in which a temperature is controlled by a temperature control process and a deviation calculation process using the above-described heating/cooling device 16; however a temperature may be controlled by a temperature control process and a deviation calculation process using a heating/cooling device other than heating/cooling device 16.

The present invention takes as an first object to provide a thermal fatigue testing device in which a test piece (test body) can be heated and cooled quickly and/or uniformly. The present invention takes as a second object to provide a thermal fatigue testing device and a recording medium recorded with a program in which a faster, more accurate and more stable temperature control can be performed.

In order to achieve the first object described above, a thermal fatigue testing device according to the first embodiment includes: a gas cooling component that cools a blown gas (such as air, nitrogen or carbon dioxide) to a predetermined temperature or less, and that is provided with a heat insulating member at an outer side surface thereof; a tube member, having a gas flow path formed therein from a first end to a second end, and provided at an outer side surface thereof with a heat radiating portion from the second end to a first intermediate portion, and being connected with the gas cooling component at the first end side, and a test body being arranged at the second end side; and a heat generating body provided in the gas flow path between the first end and a second intermediate portion, that heats a gas flowing through the gas flow path.

According to the thermal fatigue testing device of the first embodiment, it is possible to blow a gas to a test body, the gas having a temperature within a range from a temperature cooled to a predetermined temperature or less, to a temperature of air heated by a heat generating body.

According to the thermal fatigue testing device of the first embodiment, owing to a heat insulating member provided at an outer side surface of a gas cooling component, it is possible to suppress the influence of a temperature of an outer portion of a gas cooling component on a temperature of a gas cooled by the gas cooling component, and thereby it is possible to cool a gas more quickly and to a lower temperature.

According to the thermal fatigue testing device of the first embodiment, since a heat generating body is provided in a gas flow path between a first end and second intermediate part, an air flow is obstructed and a flow speed distribution increases, thereby generating a large temperature distribution at the second intermediate part, but the since heat generating body is not provided from the second intermediate part to a second end in the gas flow path, an air flow is not obstructed and a flow speed distribution decreases, and a heat exchange occurs between air at different temperatures in the gas flow path from the second intermediate part to the second end, thereby reducing an air temperature distribution at the second end. As a result, it is possible to perform uniform and stable heating or cooling with respect to a test body.

According to the thermal fatigue testing device of the first embodiment, since a heat radiating portion is provided at an outer side surface from a second end to a first intermediate portion, compared to a case in which an insulating material is provided at the outer side surface, it is possible to accelerate an increase or a decrease in a temperature of gas in a gas flow path which is to be changed by a heat generating body. For example, when gas cooled by a gas cooling component is not heated by a heat generating body, then after blowing the cooled gas to a test body, in order to increase the temperature of gas blown to the test body, gas cooled by the gas cooling component is heated by the heat generating body, and if an insulating material is provided, the temperature of the insulating material stays low and an increase in temperature of gas blown to the test body is suppressed and the speed at which a temperature increases is reduced. By contrast, according to the thermal fatigue testing device of the first embodiment, since a heat radiating body is provided at an outer side surface from a second end to a first intermediate part, the suppression of an increase in temperature of a gas blown to the test body can be eliminated. As a result, owing to the thermal fatigue testing device of the first embodiment, control can be performed such that a change in temperature of gas blown to the test body is accelerated.

As explained above, owing to the thermal fatigue testing device of the first embodiment, it is possible to heat or cool a test body more quickly and uniformly.

A refrigeration portion that keeps gas cooled by the gas cooling component cold may also be provided, and the tube member may be connected at a first end side to the gas cooling component via the refrigeration portion. Thereby, a temperature of cooled gas is more stable when the gas flows through the gas flow path of the tube member.

The tube member preferably includes a material that can transmit light and heat, but that has a low thermal conductivity, such as glass. Thereby, heat loss from the tube member can be suppressed and fast and efficient heating (or heating and cooling) can be realized.

In other words, to achieve the first object, the thermal fatigue testing device according to a second embodiment includes: a gas cooling component that quickly cools a blown gas to a predetermined temperature or less, and a heating component, having a gas flow path formed therein from a first end to a second end, through which gas flows from the first end to the second end, the gas cooling component being connected directly to the first end, a test body being arranged at the second end, the heating component being provided with a heat generating body arranged in the gas flow path that heats the gas flowing through the gas flow path, a heat radiating portion being provided at an outer side surface of the gas flow path at which the heat generating body is arranged, a wall surface of the radiating portion including a glass tube, and the heating component quickly heating to a predetermined temperature for gas which has been cooled by the gas cooling component.

According to the thermal fatigue testing device of the second embodiment, a gas that has been quickly temperature-adjusted to a temperature within a wide range from a predetermined cooled temperature or less to a maximum temperature achieved by heating with a heat generating body, can be blown to a test body.

According to the second embodiment of the present invention, a heat radiating portion may be provided at 80% or more of an outer side surface of a gas flow path provided with a heat generating body. Thereby, compared to a case in which a heat insulating member is provided at the outer side surface, it is possible to accelerate an increase or a decrease in a temperature of a gas in the gas flow path which is to be changed by the heat generating body. For example, when gas cooled by a gas cooling component is not heated by a heat generating body, then after blowing the cooled gas to a test body, in order to increase the temperature of gas blown to the test body, gas cooled by the gas cooling component is heated by the heat generating body, and if an insulating material is provided, the temperature of the insulating material stays low and an increase in temperature of gas blown to the test body is suppressed and the speed at which a temperature increases is reduced. By contrast, according to the thermal fatigue testing device of the second embodiment, since a heat radiating portion is provided at 80% or more of an outer side surface of a gas flow path provided with a heat generating body, the suppression of an increase in temperature of a gas blown to the test body can be eliminated. As a result, owing to the thermal fatigue testing device of the second embodiment, control can be performed such that a change in temperature of gas blown to the test body is accelerated.

As explained above, according to the thermal fatigue testing device of the second embodiment, it is possible to quickly heat or cool a test body.

The thermal fatigue testing device of the second embodiment may further include a constant-temperature portion including a high thermal conductivity member having a thermal conductivity of a predetermined value or greater and formed so as to surround the test body, such that gas blown from the second end is temporarily trapped around the test body. Further, the test body may be covered by the high thermal conductivity member. Thereby, since heat of a gas blown to a test body is transmitted quickly and uniformly to the entirety of a test body, it is possible to heat or cool the entirety of a test body quickly and uniformly simply by blowing gas to a single portion of the test body. This effect is considerable, and since the temperatures of a side of a test body to which gas is blown, and a side of a test body to which gas is not blown can be made uniform quickly, it is possible to heat or cool quickly and uniformly a large test body by blowing gas only from one direction. Since there is no need to blow gas from plural directions, it is possible to simplify a device configuration.

Further, a cold insulator portion that keeps gas cooled by the gas cooling component cold may be further provided, in which the heating component is connected with the cooling component at the first end via the cold insulator portion. Thereby, a temperature of cooled gas is more stable when the gas flows through a gas flow path of the tube member.

The heating component preferably includes a material that can transmit light and heat, but has a low thermal conductivity, such as glass. Thereby, heat loss from an outer side surface can be suppressed and fast and efficient heating (or heating and cooling) can be realized.

In the thermal fatigue testing device of the first and second embodiments, a heat generation control component may be provided that controls a heat generation amount of the heat generating body based on a measured temperature data.

The thermal fatigue testing device of the first embodiment and the second embodiment may further include a constant-temperature portion formed of a high thermal conductivity material having a thermal conductivity of a predetermined value or higher, that surrounds the test body such that gas blown from the second end is temporarily trapped around the test body. Further, the test body may be covered with the high thermal conductivity material. Thereby, since heat of a gas blown to a test body can be more quickly and more uniformly transmitted to the entirety of the test body, it is possible to heat or cool the entirety of the test body quickly and uniformly simply by blowing gas to a portion of the test body. This effect is considerable, and since the temperatures of a side of the test body to which gas is blown, and a side of the test body to which gas is not blown can be made uniform quickly, it is possible to heat or cool quickly and uniformly a large test body by blowing gas only from one direction. Since there is no need to blow gas from plural directions, it is possible to simplify a device configuration.

In the first embodiment or second embodiment, the gas cooling component may include a vortex tube. If a vortex tube is used, a gas can be cooled quickly to a predetermined temperature in a short period of time in which the gas flows through the gas cooling component. Further, a different gas cooling component may be used as long as it can also cool a gas to a predetermined temperature in a short period of time in which the gas flows through the gas cooling component.

In the thermal fatigue testing device of the first embodiment or second embodiment, the high thermal conductivity material may be aluminum foil or copper foil.

In order to achieve the above-described second object, a third embodiment of the present invention includes: a tube member, having a gas flow path formed therein from a first end to a second end, such that gas flows from the first end through the gas flow path, and having a test body arranged at a second end side thereof, a heat generating body provided in the gas flow path that heats gas flowing through the gas flow path; a test body temperature detection component that detects a temperature of the test body; a deviation calculation component that, based on time-series data of target temperatures for changing a temperature of the test body to between predetermined upper and lower limits according to a time-series, calculates, at regular intervals of a predetermined number of cycles, at least one of a deviation between an upper limit temperature of the test body indicated by a detection signal from the test body temperature detection component and an upper limit temperature indicated by a time-series data of the target temperature, or a deviation between a lower limit temperature of the test body indicated by a detection signal from the test body temperature detection component and a lower limit temperature indicated by a time-series data of the target temperature; a correction component that, based on the time-series data of the target temperature, and the deviation calculated by the deviation calculation component, corrects the current target temperature of the test body using a first correction value which is based determined on the deviation; a correction value calculation component that, based on a deviation between a temperature of the test body detected by the test body temperature detection component, and the target temperature corrected by the correction component, calculates a second correction value for further correcting the target temperature; a derivation component that, based on a previously obtained relationship that relates a temperature difference between a temperature of the test body and a temperature of a gas blown to the test body to a temperature gradient of a target temperature indicated by time-series data of the current target temperature, derives a temperature difference between a temperature of the test body and a temperature of a gas blown to the test body that corresponds to a temperature gradient of a target temperature indicated by time-series data of the current target temperature; a target temperature calculation component that, based on a target temperature corrected by the correction component, the second correction value, and the temperature difference derived by the derivation component, calculates a target temperature of a gas blown to the test body; and a heat generating body control component that, based on a previously determined relationship between a temperature of a gas blown to the test body and a temperature of a gas at a heat generating body final end portion, and based on a target temperature calculated by the target temperature calculation component, derives a temperature of gas at the heat generating body final end portion that corresponds to a target temperature, and controls an amount of heat generation from the heat generating body to achieve the derived temperature.

The thermal fatigue testing device according to the third embodiment derives a temperature difference between a temperature of a test body and a temperature of gas blown to the test body that corresponds to a temperature gradient of a current target temperature represented in a time series data of target temperatures. Then, a target temperature of gas blown to the test body is calculated taking into consideration the derived temperature difference, and based on a previously obtained relationship between a temperature of gas blown to the test body and a temperature of gas at a heat generating body final end portion, and also based on the calculated target temperature of gas blown to the test body, a gas temperature of the heat generating body final end portion that corresponds to the target temperature is derived, and a heat generation amount of the heat generating body is controlled so as to achieve the derived temperature. Since the target temperature of gas blown to the test body is calculated from a target temperature of the test body, and a gas temperature of the heat generating body final end portion is derived from a previously obtained relationship between a temperature of gas blown to the test body and a temperature of gas at the heat generating body final end portion, and the heat generation amount of the heat generating body is controlled accordingly, a target temperature of the test body can be accurately implemented, and a temperature of the test body can quickly and accurately become a target temperature represented in a time-series data of target temperatures. Moreover, since a movement of heat that causes a temperature change of the test body is in principle generated in proportion to a difference between a temperature of gas blown to the test body and a temperature of the test body, by using a temperature of gas blown to the test body as a physically significant intermediate parameter, temperature control is performed based on basic principles, and thereby stable temperature control can be realized.

In order to achieve the above-described second object, the present invention provides a storage medium readable by a computer, the storage medium storing a program of instructions executable by the computer to perform a function as components. The components includes: a deviation calculation component that, with respect to a test body which is arranged at a second end side of a tube member having a gas flow path formed therein from a first end to a second end, such that gas flows from the first end through the gas flow path, and having the test body arranged at a second end side thereof, based on time-series data of target temperatures for changing a temperature of the test body to between predetermined upper and lower limits according to a time-series, calculates, at regular intervals of a predetermined number of cycles, at least one of a deviation between an upper limit temperature of the test body indicated by a detection signal from a test body temperature detection component that detects a temperature of the test body, and an upper limit temperature indicated by a time-series data of a target temperature, or a deviation between a lower limit temperature of the test body indicated by a detection signal from the test body temperature detection component and a lower limit temperature indicated by a time-series data of the target temperature; a correction component that, based on the time-series data of the target temperature, and the deviation calculated by the deviation calculation component, corrects a current target temperature of the test body using a first correction value which is based determined on the deviation; a correction value calculation component that, based on a deviation between the temperature of the test body detected by the test body temperature detection component, and the corrected target temperature determined by the correction component, calculates a second correction value to further correct the corrected target temperature; a derivation component that, based on a previously obtained relationship that relates a temperature difference between a temperature of the test body and a temperature of a gas blown to the test body to a temperature gradient of a target temperature indicated by time-series data of the current target temperature, derives a temperature difference between a temperature of the test body and a temperature of a gas blown to the test body that corresponds to a temperature gradient of a target temperature indicated by time-series data of the current target temperature; a target temperature calculation component that, based on the corrected target temperature determined by the correction component, the second correction value, and the temperature difference derived by the derivation component, calculates a target temperature of a gas blown to the test body; and a heat generating body control component that, based on a previously determined relationship between the temperature of the gas blown to the test body and a temperature of a gas at final end portion of a heat generating body provided in the gas flow path that heats gas flowing through the gas flow path, and based on the target temperature calculated by the target temperature calculation component, derives a temperature of gas at the heat generating body final end portion that corresponds to the target temperature, and controls an amount of heat generation from the heat generating body to achieve the derived temperature.

According to the program of the present invention, based on the same principles as the thermal fatigue testing device of the third embodiment, a target temperature of the test body can be accurately implemented, and a temperature of the test body can more quickly, more accurately, and more stably become a target temperature represented in a time-series data of target temperatures.

In order to achieve the above-described first object, a fourth embodiment of the present invention includes a gas supply component having a gas flow path formed therein from a first end to a second end, through which blown gas flows from the first end to the second end, a test body being arranged at a second end side; and a constant-temperature portion including a high thermal conductivity member having a thermal conductivity of a predetermined value or greater and formed so as to surround the test body, such that gas blown from the second end is temporarily trapped around the test body. Thereby, heat of a gas blown to a test body can be efficiently transmitted to the entirety of a test body, and heat radiation from the test body can be prevented. As a result, fast heating or cooling of the test body can be achieved. Further, since a temperature of a constant-temperature portion is uniform owing to a high thermal conductivity material, a temperature of the test body also becomes uniform.

In order to achieve the above-described first object, a fifth embodiment of the present invention includes a gas supply component having a gas flow path formed therein from a first end to a second end, through which blown gas flows from the first end to the second end, a test body being arranged at a second end side, in which the test body is covered with a high thermal conductivity member having a thermal conductivity of a predetermined value or greater. Thereby, since heat of a gas blown to a test body can be more quickly and more uniformly transmitted to the entirety of the test body, it is possible to heat or cool the entirety of the test body quickly and uniformly simply by blowing gas to a portion of the test body. This effect is considerable, and since the temperatures of a side of the test body to which gas is blown, and a side of the test body to which gas is not blown can be made uniform quickly, it is possible to heat or cool quickly and uniformly a large test body by blowing gas only from one direction. Since there is no need to blow gas from plural directions, it is possible to simplify a device configuration. Further, the gas of the fourth embodiment and the fifth embodiment may be one that is used for cooling and heating, and may be created at a general cooling component or heating component and supplied from a first end. If a vortex tube is used, a gas can be cooled quickly to a predetermined temperature in a short period of time in which the gas flows through the gas cooling component. Further, a different gas cooling component may be used as long as it can also cool a gas to a predetermined temperature in a short period of time in which the gas flows through the gas cooling component.

As explained above, the thermal fatigue testing device of the first embodiment has the effect that it is possible to heat or cool a test body more quickly and more uniformly.

Further, the thermal fatigue testing device of the second embodiment has the effect that it is possible to heat or cool a test body more quickly and more uniformly.

Still further, the thermal fatigue testing device and program of the third embodiment has the effect that it is possible to perform a faster, more accurate and more stable temperature control.

Moreover, the thermal fatigue testing device of the fourth and fifth embodiments have the effect that it is possible to heat or cool a test body more quickly and more uniformly.

What is claimed is:

1. A thermal fatigue testing device, comprising:
   a gas cooling component that cools a blown gas to a predetermined temperature or less, and that is provided with a heat insulating member at an outer side surface thereof;
   a tube member, having a gas flow path formed therein from a first end to a second end, and provided at an outer side surface thereof with a heat radiating portion from the second end to a first intermediate portion, and being connected with the gas cooling component at the first end side, a test body being arranged at the second end side, and
   a heat generating body provided in the gas flow path between the first end and a second intermediate portion, that heats a gas flowing through the gas flow path.

2. The thermal fatigue testing device of claim 1, further comprising a heat generation control component that controls an amount of heat generation of the heat generating body, based on measured temperature data.

3. The thermal fatigue testing device of claim 1, further comprising a constant-temperature portion comprising a high thermal conductivity member having a thermal conductivity of a predetermined value or greater and formed so as to surround the test body, such that gas blown from the second end is temporarily trapped around the test body, wherein the test body is covered by the high thermal conductivity member.

4. The thermal fatigue testing device of claim 3, wherein the high thermal conductivity member comprises an aluminum foil or a copper foil.

5. The thermal fatigue testing device of claim 1, further comprising a cold insulator portion that keeps gas cooled by the gas cooling component cold, wherein the tube member is connected with the gas cooling component via the cold insulator portion.

6. The thermal fatigue testing device of claim 1, wherein the gas cooling component comprises a vortex tube.

7. A thermal fatigue testing device, comprising:
   a gas cooling component that cools a blown gas to a predetermined temperature or less, and
   a heating component, having a gas flow path formed therein from a first end to a second end, through which gas flows from the first end to the second end, the gas cooling component being connected directly to the first end, a test body being arranged at the second end, the heating component being provided with a heat generating body arranged in the gas flow path that heats the gas flowing through the gas flow path, a heat radiating portion being provided at an outer side surface of the gas flow path at which the heat generating body is arranged, a wall surface of the radiating portion comprising a glass tube, and the heating component heating to a predetermined temperature for gas which has been cooled by the gas cooling component.

8. The thermal fatigue testing device of claim 7, wherein the heat radiating portion is provided at 80% or more of an outer side surface of the gas flow path at which the heat generating body is arranged.

9. The thermal fatigue testing device of claim 7, further comprising a heat generation control component that controls an amount of heat generation of the heat generating body, based on measured temperature data.

10. The thermal fatigue testing device of claim 7, further comprising a constant-temperature portion comprising a high thermal conductivity member having a thermal conductivity of a predetermined value or greater and formed so as to surround the test body, such that gas blown from the second end is temporarily trapped around the test body, wherein the test body is covered by the high thermal conductivity member.

11. The thermal fatigue testing device of claim 10, wherein the high thermal conductivity member comprises an aluminum foil or a copper foil.

12. The thermal fatigue testing device of claim 7, further comprising a cold insulator portion that keeps gas cooled by the gas cooling component cold, wherein the tube member is connected with the gas cooling component via the cold insulator portion.

13. The thermal fatigue testing device of claim 7, wherein the gas cooling component comprises a vortex tube.

14. A thermal fatigue testing device, comprising:
  a gas supply component having a gas flow path formed therein from a first end to a second end, through which blown gas flows from the first end to the second end, a test body being arranged at a second end side,
  a constant-temperature portion comprising a high thermal conductivity member having a thermal conductivity of a predetermined value or greater and formed so as to surround the test body, such that gas blown from the second end is temporarily trapped around the test body, and
  a heating or cooling element to adjust the temperature of the gas.

15. A thermal fatigue testing device, comprising
  a gas supply component having a gas flow path formed therein from a first end to a second end, through which blown gas flows from the first end to the second end, a test body being arranged at a second end side, wherein the test body is covered with a high thermal conductivity member having a thermal conductivity of a predetermined value or greater, and
  a heating or cooling element to adjust the temperature of the gas.

\* \* \* \* \*